United States Patent [19]
Skinner

[11] Patent Number: 5,709,214
[45] Date of Patent: Jan. 20, 1998

[54] PD2I ELECTROPHYSIOLOGICAL ANALYZER

[75] Inventor: James E. Skinner, Bangor, Pa.

[73] Assignee: Enhanced Cardiology, Inc., Lubbock, Tex.

[21] Appl. No.: 641,944

[22] Filed: May 2, 1996

[51] Int. Cl.⁶ .................................................. A61B 5/04
[52] U.S. Cl. ........................................ 128/702; 128/731
[58] Field of Search .............................. 128/696, 702, 128/731

[56] References Cited

U.S. PATENT DOCUMENTS 5,215,099   6/1993   Haberl et al. ..................... 128/702

OTHER PUBLICATIONS

Skinner et al., Brain Dynamics, Springer–Verlag series, pp. 119–134 (1990).
Skinner et al., Chaos in the Heart, BioTechnology, vol. 8, pp. 1018–1024 (1990).
Skinner et al., The Correlation–dimension of Heartbeat Intervals, Circulation Research, vol. 68, pp. 966–976 (1991).
Molnar et al., Low–dimensional Chaos, Intern. J. Neuro., vol. 66, pp. 263–276 (1992).
Molnar et al., Correlation Dimension Changes of the EEG, Acta Biochem. Biophys. Hung., vol. 26, pp. 121–125 (1992).
Skinner et al., Application of Chaos Theory to Biology and Medicine, Integ. Physiol. and Beh. Sci., vol. 27, pp. 39–51 (1992).
Mitra et al., Low–dimensional Chaos Maps, Integ. Physiol. and Beh. Sci., vol. 27, pp. 304–322 (1992).
Skinner et al., A reduction in the Correlation Dimension of Heartbeat Intervals, Am. Heart J., vol. 125, pp. 1018–1024 (1993).

*Primary Examiner*—Scott Getzow
*Attorney, Agent, or Firm*—Hopgood, Calimafde, Kalil & Judlowe L.L.P.

[57] ABSTRACT

Disclosed is a method and a device in which electrophysiological signals are acquired and analyzed to provide a basis of prediction of clinical outcomes such as sudden cardiac death and cerebral epilepsy.

2 Claims, 8 Drawing Sheets

PD2I ELECTROPHYSIOLOGICAL ANALYZER

FIELD OF INVENTION

The invention relates to methods and apparatus for evaluating electrophysiological potentials such as from the electrocardiogram and the electroencephalogram. More specifically, the invention is a method and associated apparatus for evaluating electrophysiological potentials in a manner that will sensitively and specifically predict future pathological events such as cardiac arrhythmias and epilepsy, and monitor altered states of cognition, such as those underlying memory.

BACKGROUND

The recording of electrophysiological potentials has been available to the field of medicine since the invention of the string galvenometer. Since the 1930's electrophysiology has been useful in diagnosing cardiac injury and cerebral epilepsy. The state-of-the-art in modern medicine shows that analysis of R—R intervals observed in the electrocardiogram or of spikes seen in the electroencephalogram can predict future clinical outcomes, such as sudden cardiac death or epileptic seizures.

Such analyses and predictions are statistically significant when used to discriminate outcomes between large groups of patients who either do or do not manifest the predicted outcome, but known analytic methods are not very accurate when used for individual patients. This general failure of known analytic measures is attributed to the large numbers of false predictions; i.e. the measures have low sensitivity and specificity in their predictions. It is usually known that something "pathological" is going on in the biological system under study, but currently available analytic methods are not sensitive and specific enough to permit utility in the individual patient.

The inaccuracy problems prevalent in the art are due to current analytic measures (1) being stochastic (i.e. based on random variation in the data), (2) requiring stationarity (i.e. the system generating the data cannot change during the recording), and (3) being linear (i.e. insensitive to nonlinearities in the data which are referred to in the art as "chaos").

A need exists in the art for an analytic measure that (1) is deterministic (i.e. based on caused variation in the data), (2) does not require stationarity (i.e. actually tracks nonstationary changes in the data), and (3) is sensitive to chaotic as well as nonchaotic, linear data.

Many theoretical descriptions of dimensions are known such as "D0" (Hausdorff dimension), "D1" (information dimension), and "D2" (correlation dimension). Packard et al., Geometry from a time series, Physical Review Letters, 45:712–716 (1980), first suggested that the dimension of the generator could be reconstructed from a time-series sample of data from only one of the variables. Takens, Detecting strange attractors in turbulence, Lecture Notes in Mathematics, 898:366–381 (1981) provided a mathematical proof of Packard's idea, Packard et al., Id.; and Grassberger et al., Characterization of strange attractors, Physical Review Letters, 50 (5):346–349 (1983), developed a simple algorithm called "D2" for calculating the reconstructed dimension.

D2 enables the estimation of the dimension of a system or its number of degrees of freedom from an evaluation of a sample of data generated. Several investigators have used D2 on biological data (Babloyantz, Complex Systems, H. Haken (Ed.), Springer Pub., Berlin, pp. 116–122 (1985); Albano et al., Dimensions and Entropies in Chaotic Systems, G. Mayer-Kress (Ed.), Springer Pub., Berlin, pp. 231–240 (1986). However, Mayer-Kress et al., Dimensional analysis of non-linear oscillations in brain, heart and muscle, Mathematical Biosciences, 90:155–182 (1988), showed that the presumption of data stationarity cannot be met.

Farmer et al., Dimension of chaotic attractors, Physica D., 7D:153–180 (1983), proposed the Pointwise Scaling Dimension or "D2i" which Mayer-Kress et al., Ida, states was less sensitive to the nonstationarties inherent in data from the brain, heart or skeletal muscle. Mayer-Kress et al., Id., state that D2i is perhaps a more useful estimate of dimension for biological data than the D2, but still has considerable errors of estimation that might be related to data nonstationarities.

Skinner et al., The correlation-dimension of the heartbeat is reduced by myocardial ischemia in conscious pigs, circulation Research, 68:966–976 (1991), describes the Point Correlation Dimension algorithm (PD2) and shows that it is superior to both the D2 and D2i in detecting changes in dimension in nonstationary data (i.e. data made by linking subepochs from different chaotic generators).

Rapp, A Guide to Dynamical Analysis, Integrative Physiological and Behavioral Science, 29:3 (1994), lists the ways one can get false impressions about detecting chaos in biological systems. Uncontrolled shifts in the generator which are nonstationarity invalidate measures of the correlation dimension. Furthermore filtered noise can be low-dimensional, have high determinism and contain at least one positive Lyapunov exponent. Oversampling of data can produce spurious low-dimensional estimates due to the presence of too many near neighbors. Under-sampling can produce stroboscopic effects that also produce spurious results. Nonstationarity, filter-effects, the presence of noise, a high or low digitization rate, short data epochs are all problems in data acquisition that can lead to spurious results.

Theiler, Serious dimension from correlation, algorithms applied to limited time-series data, Physical Reviews, A 34:2427–2432 (1986), describes an algorithm that eliminates near-neighbor effects. Theiler et al., Testing for nonlinearity in time series: the method of surrogate data, Physica D., 58: 77–94 (1992), teaches a way to convert the biological data into filtered noise of the same bandpass so that the analysis of the biological data can be compared to this surrogate to rule out the possibility that the data are filtered noise. Others who have used data surrogates as controls include, Schiff et al., Discriminating Deterministic versus Stochastic Dynamics in Neuronal Activity, Integrative Physiological and Behavioral Science, 29:3 (1994).

Skinner et al., The Point Correlation Dimension: Performance with Non-Stationary Surrogate Data and Noise, Integrative Physiological and Behavioral Science, 29:3 (1994), discloses an algorithm for calculating the correlation dimension at a small point in the data series. This algorithm resolves two issues at once, (1) it is insensitive to data nonstationarities, and (2) it enables dimension to be calculated as a function of time, thus revealing where the nonstationary shifts are.

New tabulations suggests that although many earlier biological studies may not have been properly conducted or adequately controlled, the original interpretations may have been correct. Despite the potential shortcomings in data acquisition and analysis, such as the types mentioned by Rapp, Id., there is a certain "robustness" in the measures.

Newer measures such as Dynamic Determinism described in Elbert et al., Chaos and physiology, Physiological Reviews, 74:1–47 (1994) and PD2 are indeed more sensitive in a statistical sense (i.e. produce greater F values), but the older measures such as D2 and Entropy discriminated between the experimental and control groups, as shown in Table 1, below.

TABLE 1

Comparison of several measures of low-dimensional chaos in their ability to discriminate between control and experimental EEG data and between control EEG data and their surrogate controls. All calculations were made on the same data and are listed as the mean:standard deviation.

| | Experimental EEG Data | Control EEG Data | Filtered Noise Surrogate | Chaos (Lorenz) Surrogate |
|---|---|---|---|---|
| Older Measures: | | | | |
| D2 (Grassberger) | 7.6:2.8* | 9.0:2.5 | 9.1:3.1$^{NS}$ | 2.06:0.01$^\#$ |
| Entropy (Kolmorogrov) | −527:152* | −420:59 | | |
| Newer Measures: | | | | |
| PD2 (Skinner) | 5.6:0.7** | 6.4:0.2 | 7.1:3.2** | 2.08:0.04$^\#$ |
| Dynamic Determinism (Elbert) | .334:.012** | .320:.008 | .303:.002** | .977:.001$^\#$ |

The Experimental EEG Data were recorded from brainstem-damaged decerebrate humans, and the Controls were recorded from normals; the Lorenz data was generated to have approximately the same 1/f - shaped envelope of the power spectrum as that of the EEG of the controls. Skinner et al., Id.
Table 1 LEGEND
*$P < 0.05$ (F = 7.3 for D2; F = 4.2 for Entropy; df = 1,17)
**$P < 0.001$ (F = 11.0 for PD2; F = 11.5 for Dyn. Determ.; df = 1,17)
$^{NS}$"Not significant"
$^\#P < 0.01$ (t > 5, df = 17)

The robustness presumably occurs because the errors caused by either poor data acquisition or analysis are systematic, and the errors are of the same amount and in the same direction in both the experimental and control groups. The discrimination would not be apparent if the data contained noise because both of the dimensions would be as high as the filtered noise surrogate, and they are not. The data must therefore contain a geometrical structure in phase space that could only be explained by their being made by a chaotic generator of relatively low dimension.

Thus, a need exists in the art for an improved analytic measure that is deterministic, does not require stationarity and is sensitive to chaotic as well as nonchaotic, linear data.

OBJECTS AND SUMMARY OF THE INVENTION

Accordingly, an object of the invention is to provide a method and associated apparatus for evaluating electrophysiological potentials (such as from electrocardiograms and electroencephalograms) with a sensitivity and specificity to predict future pathological events such as fatal cardiac arrhythmias and epilepsy, and monitor altered states of cognition such as those underlying memory.

More specifically, the objects of the invention comprise methods and associated apparatuses for (1) detecting deterministic low-dimensional excursions in nonstationary heartbeat intervals made from the electrocardiogram as harbingers of fatal cardiac arrhythmias; (2) detecting dynamics of QT vs RR-QT jointly-plotted heartbeat subintervals, in a previously observed exclusion area, as harbingers of fatal cardiac dynamical arrhythmias; (3) detecting persistent alterations in the deterministic dimensional reconstructions made from the nonstationary electroencephalogram as a measure of altered cognitive state; and (4) detecting an enlarged variance in the deterministic dimensional variations in electroencephalograhpic potentials as a harbinger of early paroxysmal epileptic activity.

The present invention uses an analytic measure that is deterministic and based on caused variation in data; does not require stationarity and actually tracks nonstationary changes in the data; and is sensitive to chaotic as well as nonchaotic, linear data. This analytic measure, the improved Point Correlation Dimension ("PD2i"), is based on previous analytic measures that are collectively, the algorithms for estimating the correlation dimension, but the novelty of the present dislcosure is that it is insensitive to data nonstationarities. Because of this feature, the PD2i can predict clinical outcomes with high sensitivity and specificity that the other measures cannot.

Controlled, double-blinded, randomized studies in human patients (see below) empirically supports the present invention. The invention incorporates the novel PD2i algorithm, manifested in software, in a conventional computer receiving input from a conventional digitizer attached to a conventional analog electrophysiological amplifier. The methods and apparatus of the invention have heretofore been unavailable for useful purposes in medicine and physiology. Because the uniqueness of the methods and apparatus are based on the uniqueness of the PD2i algorithm, this latter component will be the focus of this Summary of Invention.

To understand the PD2i algorithm, an understanding of algorithms already known and in the public domain is required. The correlation dimension (D2) of a time-series is defined as $C(r,n)\sim r$ expD2 where $C(r,n)$ is the cumulative number of all rank-ordered vector-difference lengths within a range (r) and n is the number of vector-difference lengths (the "~" sign means, "scales as"). The term, $C(r,n)$ is known as the correlation integral.

Vector-differences are made as follows, (1) a reference vector is constructed that begins at a specific point, i, in the data (i.e. the i-vector); it is made by taking a specified number (m−1) sequential time-steps in the data stream that are of a fixed length, Tau; each data value encountered by the time-steps is used as one coordinate of the m-dimensional vector; (2) A different vector (j-vector) is then made by beginning at a different starting point, but using the same number of Tau-steps; (3) the difference vector is made by subtracting the i-vector and j-vector from one another.

This subtraction can be calculated by three methods (norms) each of which produces approximately the same scaling result, (1) the L-one norm ("as the crow flies"), (2) the L-zero norm ("taxi cab route"), or (3) the L-infinity norm ("longest leg of taxi route"). For example, c=square-root of a exp2+b exp2 (L-zero), c=a+b (L−1), or c=a or b, whichever is larger (L-infinity). For calculation speed, the L-infinity norm is the fastest.

Normally the reference i-vector is kept at a fixed place, while all of the j-vectors are made. Each j-vector starts at the first data point, which is its first coordinate, and then takes m-1 Tau-steps from this point to select its other coordinates The starting data point is then moved to the next data point (one point to the right) and the second j-vector is made. The starting point is moved sequentially throughout the data series until all j-vectors for that m have been made. The j-vector identical to the fixed i-vector is excluded and the last reference vector in the data series is m×Tau points from the end of the series (i.e., there are not enough data points to make any more j-vectors).

After making the i–j vector differencs, the i-vector is moved one point to the right, the already made j-vectors are recalled, and the i–j vector differences again calculated. This is done for each embedding dimension from m=1 to m=m-max, where m-max=twice the expected D2+1.

The distinguishing feature of the D2 algorithm is that all possible vector-differences (i.e. at a given embedding dimension) are made for the correlation integral before the next step in the calculation is taken. That is, both the i-vectors and the j-vectors run through the whole data series, with each combination contributing a different value to the i–j vector-difference set. After completion, the absolute values of the vector-difference lengths, for each m, are rank-ordered, creating a set of numbers, the D2-set, for that embedding dimension. It is the numbers in the D2-set that distinguishes among the three algorithms for estimating the correlation dimension.

The next step in the D2 algorithm is to make a cumulative histogram of these rank-ordered vector-difference lengths created at each m. A range value (r, i.e. bin-width), that initially includes only the smallest vector-difference length, is continuously incremented in size and the corresponding number of vector-difference lengths in each range is continuously counted. This cumulative histogram, C, will have a shape related to the size of the incremental values of r and the total number of vector difference-lengths, n.

The next step is to plot the cumulative histogram on a log—log scale and then measure the slope of a linear scaling region that will appear. This scaling region will appear only if the data are valid (i.e., stationary and lengthy) and thus fulfill the model, where $C(r,n) \sim r$ expD2, or D2~log $C(r,n)$/log r. Note that the latter is a linear slope in the log—log plot. This scaling region requires a criterion for determining its linearity, as finite data will result in a D2-set that is never absolutely linear when plotted cumulatively on a log—log scale.

As the value of m is incremented, the corresponding slope will also increment, thus yielding slope and m pairs. The maximum value of m is selected to span the size of the expected D2 value (that is, m ranges from 1 to 2D2+1). Since biological data are normally less than 6, the maximum embedding dimension can usually be limited to 12. The number of embedding dimensions is relevant only up to the point where its increment is no longer associated with an increase in the slope of the linear scaling region (i.e. the slope converges). D2 then is the slope of the linear region at the convergent values of m.

Mathematical stationarity is presumed during the collection of data in the above D2 application, a presumption which is not tenable for biological data; the generator is constantly changing state because of its interaction with the nervous system. The "pointwise" scaling dimension (D2i) was suggested by Farmer et al., Id., to be an estimate of D2. This algorithm is perhaps less sensitive to nonstationarities, because the reference vector (i.e. the current i-vector, starting at point, i is fixed for each estimate and dominates the calculations; the j-vectors made with respect to this single reference vector will still span and probe the entire data-epoch, but they alone are the basis for the each D2-set and the log—log plots used to determine the slope and m pairs. Since the reference vector is chosen sequentially for each digitized point in the time-series, dimension is estimated as a function of time. This algorithm, like D2, presumes stationary of the data in the epoch analyzed.

In the present "point-D2" estimate of the correlation dimension (PD2i), each reference-vector (i.e. the current i-vector at a given m) remains fixed, while each of the j-vectors run through the whole data series. But for the PD2i, the j-vectors that will contribute to the small log-r values must arise from a subepoch that manifests scaling characteristics similar to those surrounding the i-vector.

Basically the PD2i reference vector seeks its own subspecies of stationary data with which to make the vector-difference lengths. This occurs by a process that involves, (1) the plot length (PL) of the small log-r values in the scaling region (i.e. as observed in the log—log plot of the cumulative histogram of the rank-ordered vector difference lengths vs the range); (2) the linearity criterion (LC) for this scaling region; and (3) the convergence criterion (CC) of the slope of this scaling region vs the embedding dimension. This algorithm is fast and can be performed, for example, online for the analysis of 4,000 heartbeat intervals using a 486-CPU. Part of the success of PD2i revolves around the rejection of values that do not result in linear scaling and clear convergence; these rejections also eliminate PD2i estimates that could result from contamination of the small log-r values (i.e. by other nonstationary subepochs, noise or artifacts in the data). Contamination by cardiac arrhythmias is also eliminated.

The model for the PD2i is $C(r,n,ref\star) \sim r$ expD2, where ref$\star$ is an acceptable reference point from which to make the various m-dimensional reference vectors, because these will have a scaling region of maximum length PL that meets the linearity (LC) and convergence (CC) criteria. Because each ref$\star$ begins with a new coordinate in each of the m-dimensional reference vectors and because this new coordinate could be of any value, the PD2i's may be independent of each other for statistical purposes.

The value of Tau is irrelevant if the number of points in the time-series is infinite, a condition which is never approached for biological data. A conventional way of determining the size of the Tau-step is to calculate the first zero-crossing of the autocorrelation function of the data. When multiple peaks are present in the power spectrum (i.e. the fast Fourier transform of the autocorrelation function), as is the case for the Lorenz time-series, Tau should be selected as the number of digitized values in a quarter-cycle of one of the higher dominant frequencies. One should be cautious about Tau selection when nonstationarities arise in finite data, for each subepoch may require a different Tau for adequate sampling of its attractor. That is, the autocorrelation function and power spectrum should be evaluated separately for each subepoch.

"Stationarity" means that the data generator cannot change during data acquisition. That is, the independent variables in the generator (degrees of freedom) cannot change. For example, changing from a sine wave generator to a Lorenz generator during data generation would create a nonstationarity. For biological data, in which the generator cannot be directly known, this means evaluating the data in a manner that would be sensitive to a change in state of the generator. This is usually done with a measure, such as the mean, standard deviation or fast Fourier transform that is run, as a subepoch window, through the data. If the values change in a statistically significant manner, then the data must be presumed to be nonstationary.

For example, in RR interval data, the occurrence of a cardiac arrhythmia is a nonstationarity. For all stochastic measures these arrhythmias must be removed before RR interval means, standard deviations or power spectra can be measured. For the Point Correlation Dimension, however, the arrhythmias will produce high dimensional shifts when they are in the "point" of the brief interval of the reference vector and these can easily be separated out of the mean PD2i for the control and experimental groups. This feature of PD2i enables RR interval data from cardiac patients to be evaluated without having to detect and remove the cardiac arrhythmias.

The three dimensional algorithms were explained in detail above. Next, the set of rank-ordered vector-difference lengths (i.e. the D2-set), a quantitation used in each of the algorithms is referred to. As explained above, the essential difference among the dimensional algorithms is how the vector-difference lengths are selected for further evaluation. The classical algorithm (D2) of Grassberger et al., Id, uses all possible vector-difference lengths, whereas the pointwise scaling dimension (D2i) of Farmer et al., Id., uses only a subset of them, those made with respect to a fixed reference vector. In contrast, the present point correlation dimension algorithm (PD2i) selects a subset made from a subepoch of the same stationary type as the one in which the reference vector is located. After selecion of the rank-ordered vector-difference lengths, the algorithms are essentially the same. Each examines the log—log plot of the cumulative histogram of the rank ordered vector-difference lengths for the linear scaling region that determines the correlation dimension. In all cases, this scaling region must meet a criterion for linearity and then another for the convergence of the slope of this scaling region with increasing embedding dimensions.

The problem addressed by the PD2i algorithm is how to make the D2-set selections and the rest of the calculations quickly and in a manner that, in the limit, will produce values identical to those of the classical correlation dimension, D2. One of the strategies used by the PD2i algorithm to seek subepochs with the same scaling properties as those surrounding the reference vector is to examine only the small log-r values (i.e. those numerous, small, values in the log—log plot). It is these small values, because of their number, that primarily determine the scaling relationship that defines the correlation dimension, that is, if data oversampling or other forms of contamination have not occurred. The sources of error will be discussed below.

The PD2i algorithm limits the range of the small log-r values over which linear scaling and convergence are judged by the use of a parameter called, Plot Length. The value of this entry determines for each log—log plot, beginning at the small log-r end, the percentage of points over which the linear scaling region is sought.

In nonstationary data, the small log-r values between a fixed reference vector (i-vector) in a subepoch that is a sine wave, when subtracted from multiple j-vectors in a Lorenz subepoch, will not make many small vector-difference lengths, especially at the higher embedding dimensions. That is, there will not be abundant small log-r vector-difference lengths relative to those that would be made if the j-vector for the Lorenz subepoch was instead in a sine wave subepoch. When all of the vector-difference lengths from the nonstationary data are mixed together and rank ordered, only those small log-r values between subepochs that are stationary with respect to the one containing the reference vector will contribute to the scaling region, that is, to the region that will be examined for linearity and convergence. If there is significant contamination of this small log-r region by other nonstationary subepochs, then the linearity or convergence criterion will fail and that estimate will be rejected from the PD2i mean.

The oversampling of data, for example, by using a digitizing rate greater than that required for resolving the high-frequency components, will produce a spurious low-dimensional slope in the small log-r region that results from too many near neighbors having nearly the same j-vector as that of the reference i-vector. To safeguard against oversampling, one could use the Theiler "window" explained in Theiler, *Spurious dimension from correlation algorithms applited to limited time-series date.*, Physical Reviews A 34:2427-2432 (1986). This algorithm precludes the small vector-difference lengths between near neighbors from spuriously overwhelming the small log-r region in the cumulative histogram. Most of the spurious values produced by over-sampling will result in a very small slope, so if a telltale "belly" is not seen in the small log-r values, then the Theiler "window" may not be necessary and calculation speed may therefore be maintained. For cardiac or neuronal interval-data, one does not need to worry about this problem, for oversampling cannot occur.

There is another instance in which this small log-r region can become contaminated, when dimension and amplitude change at the same time, for example, during EEG desynchronization. This is because the small log-r values are usually contributed to the D2-set by both large amplitude differences and by small amplitude differences. If the signal suddenly becomes small, then all differences will be small and these will contaminate the small log-r contributions made by the larger amplitude signal. A strategy for eliminating this contamination is to use a large number of bins in the small log-r region (i.e. 1000), and then to look carefully for different scaling regions attributable to each of the two signals.

The subepoch that the reference vector is in dictates the stationarity of the species being examined; that is, it determines what small log-r values will be used as the basis for the calculation of the PD2i. For stationary data, each PD2i (where i stands for each serial point in the whole data epoch) will show variation around a mean. This variation is due to the individualized dominance of the reference-vector coordinates, as all of the j-vectors (the comparison vectors for making the vector-difference lengths) remain the same for each PD2i. So, only the i-vectors (i.e. the series of reference vectors) contribute to this PD2i variation.

In the correlation integral for the D2 algorithm (i.e. log C(r,n) vs log r, in stationary data) the slope in the linear scaling region, slope D2, is the mean of slope i+error i, where slope i is based on the set of vector-difference lengths for a fixed reference vector at point i and error i is its deviation from slope D2; note that mean error i=0 within the set of vector-difference lengths and represents the dominance effect specific to each reference vector beginning at data-point i. In the Pointwise Dimension algorithm (D2i), each slope found is slope i; it deviates from D2 also by error i. Therefore, mean slope i, as i approaches the length of the vector-difference set, approaches D2. This same argument holds for the PD2i algorithm, that is, if it is performed on stationary data.

Thus, the mean PD2i algorithm can produce the same result as mean D2i (and D2), but what if the data are nonstationary? This is where a novel feature of PD2i manifests itself.

The following details of the algorithm explain some important parts of the source code for the PD2i algorithm and are necessary for understanding how the algorithm works.

Speed of Calculation:

The MXARAY used to count the vector difference lengths is a rapid way to form the correlation integral. It is layed out as an embedding dimension vs vector-difference length array with a counter at each matrix location. It quickly makes the correlation integral for each embedding dimension.

The use of the L-infinity norm is a rapid way to calculate the resultant vector-difference lengths that are entered into the MXARAY. The use of 250 bins for the log-r axis, using either autoscaling (amplitude sensitive during dimensional changes) or no autoscaling (less sensitive to amplitude changes during dimensional changes) was initiated to speed calculation. Because of time-series amplitude-sensitivity, this faster version of the algorithm PD2-03.exe) was replaced in favor of the version using 1000 bins for the log-r axis (PD2-02.exe). To speed up the calclations using this larger number of log-r bins, it was realized that the values above the linear scaling region did not have to be calculated.

At this point the algorithm is a parameter "tuned" version of the D2i algorithm.

Insensitivity to Data Nonstationarity:

It has traditionally been thought that insensitivity to data nonstationarities is due to the time-dependent bias by the dominance of the reference vector in determining the values in the correlation integral. The complete linear scaling region was the criterion used for determining the dimensional value. It has been recognized that the relative size of this linear scaling region in the correlation integral was reduced as data-ength was increased, but the full length of the linear scaling region was always used; data stationarity was still a requirement.

The PD2i algorithm introduces to the art the idea that the smallest initial part of the linear scaling region should be considered if data nonstationarities exist (i.e. as they always do in biological data). This is because when the j-vectors lie in a subepoch of data that is the same species as that the i-vector (reference vector) is in, then and only then will the smallest log-r vectors be made abundantly, that is, in the limit or as data length becomes large. Thus, to avoid contamination in the correlation integral by species of data that are nonstationary with respect to the species the reference vector is in, one skilled in the art must look only at the slopes in the correlation integral that lie just a short distance beyond the "floppy tail".

The "floppy tail" is the very smallest log-r range in which linear scaling does not occur due to the lack of points in this part of the correlation integral resulting from finite data length. Thus, by restricting the PD2i scaling to the smallest part of the log-r range above the "floppy tail," the PD2i algorithm becomes insensitive to data nonstationaraties. Note that the D2i always uses the whole linear scaling region, which will always be contaminated if nonstationarities exist in the data (see explanations associated with FIG. 1, below, for further exegesis of this point). The flow diagram for the logic of the algorithm is detailed in FIG. 2, below.

This short-distance slope estimate for PD2i is perfectly valid, for in any log—log plot of a linear region; it does not matter whether or not one uses all data points or only the initial segment to determine the slope. Thus, by empirically setting Plot Length to a small interval above the "floppy tail" (the latter of which is avoided by setting the linearity criterion, LC), nonstationarities can be tracked in the data with only a small error, an error which is due entirely to finite data length, and not to contamination by nonstationarities.

Thus, by appropriate adjustments in the algorithm to examine only that part of the scaling region just above the "floppy tail", which is determined by, (1) the Linearity Criterion, LC, (2) the Minimum Scaling criterion, MS, and (3) the Plot Length criterion, PL, one skilled in the art can eliminate the sensitivity of the measure to data nonstationarities.

This is the "trick" of how to make the j-vectors come from the same data species that the i-vector is in, and this can be proven empirically by placing a graphics marker on the i- and j-vectors and observing the markers in the correlation integral. This initial part of the scaling region is seen mathematically to be uncontaminated only in the limit, but practically speaking it works very well for finite data. This can be proven computationally with concatenated data. When the PD2i is used on concatenated subepochs of data made by sine-, Lorenz-, Henon-, and other types of known linear and nonlinear data-generators, the short scaling seqment will have vector-difference lengths made only by i- and j-vector differences that are stationary with respect to each other; that is, the errors for 1,200 point data subepochs are found to be less than 5.0% from their values at the limit, and these errors are due to the finite data length, not scaling contamination.

DESCRIPTION OF THE PREFERRED EMBODIMENT

PD2i ALGORITHM OUTPUT

Figure 4:
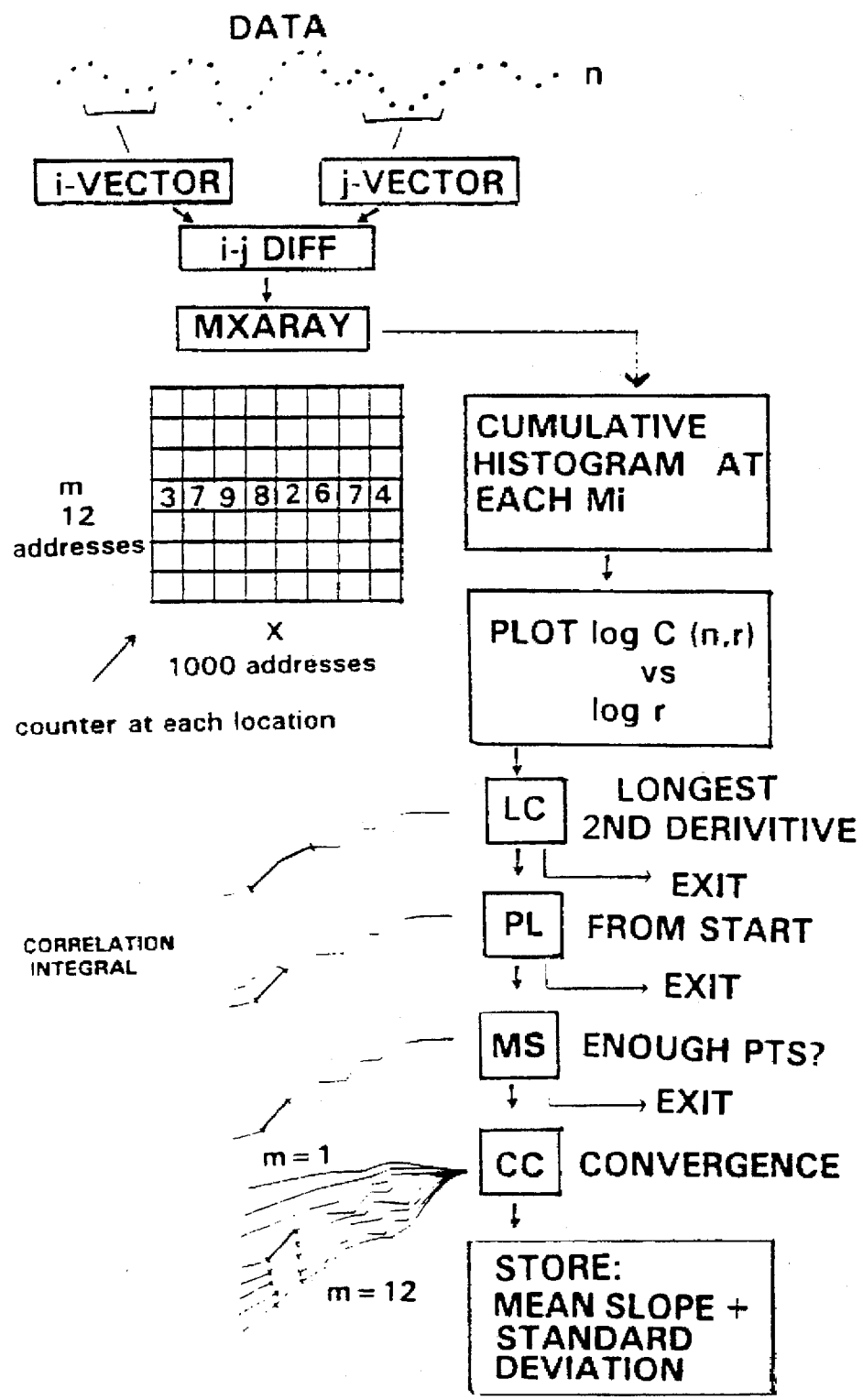
FIG. 4 shows the PD2i flow chart.

The PD2i flow chart shown in FIG. 4 begins with the data (top) and from this the i- and j-VECTORs are made and subtracted from one another (i–j DIFF). These vector difference lengths are entered, according the their value (X, 1 to 1000), into the MXARAY at the embedding dimension used (m, 1 to 12). The entry is made as an increment of a counter at each location of the MXARAY. After completion of the making of the vector difference lengths, the counter numbers (3,7,9,8,2,6,7,4. . . ) are then used to make the correlation integrals for each embedding dimension; this is done by making a cumulative histogram as a function of X, at each $m_i$, and then making the log log plot of their cumulative values vs r (PLOT log C (n,r) vs log r). Then each correlation integral is examined by the LC to find the longest segment of the second derivitive that falls within the limits of the set parameter (LC=0.30 means within a + to − deviation of 15% of the mean slope); this iterative LC test will find a range above the "floppy tail" (i.e., the smallest log-r region that is unstable because of finite data length) and run up the correlation integral until the LC criterion is exceeded (bold section of top correlation integral).

If a segment is found within the criterion, then the correlation integral scaling region is reset by the PL criterion; this value is set from the smallest data point in the correlation integral to its criterion value (e.g., 15%, bracket in second from top correlation integral). The upper and lower limits of this region are observed to see if they have at least the number of data points required by the minimum scaling (MS) criterion. And finally the selected regions of all correlation integrals (m=1 to m=12) are plotted and examined by the CC to see if convergence occurs at the higher embedding dimensions (e.g., m=9 to m=12); that is, to see if the selected regions have essentially the same slopes in which the standard deviation around the mean is within the limits set by the CC (i.e., CC=0.40 means that the deviation around the mean is within + to = 20% of the mean value). If the CC is passed, then the mean slope and standard deviation are stored to file. If failure occurs at any of the earlier criteria (LC, PL, MS), then the program will exit and move the PD2i reference vector to the next data point and then start all over. If failure occurs at the CC, the mean and standard deviation are saved without exiting, for it may be the case that later the CC is desired to be changed; i.e. the CC is a filter that determines whether or not the PD2i (i.e., the mean slope of m=9 to m=12) will be plotted in later graphical routines.

Initially, the concept of "Chaos" is characterized by a type of dynamics that is neither stable, exploding or imploding, but rather characteristically has mathematical divergence of adjacent points plotted in phase space (i.e. in an embedding dimension). Divergence means that as time goes on, the distance between the two adjacent points becomes larger and larger. This divergence was later found to be quantitated by a positive Lyapunov exponent.

None of these "Chaos" concepts, however, is concerned with an often overlooked fundamental feature, that is, they are deterministic as opposed to stochastic. Deterministic dynamics (and their measures) presume that the fine grain of the variation of data points is caused, and is not random variation due to uncertainty. The presumption of caused variation is an important distinction in signal analysis. For stochastic measures, such as the mean, standard deviation, t-value, f-value, Fourier transform, power spectrum, and so on, the presumption is that there is always random variation about a mean for any sampled data-point. The data are considered inherently noisy.

When deterministic Newtonian models failed to account for results in particle physics, Neils Bohr invented a stochastic model of the universe and this led to the field of quantum physics. The stochastic models posit random variation of all observable events (i.e. uncertainty) as a feature of the positivistic universe. Modern thinking adds that any incapacity to carry out those calculations (any uncertainty in the results of those calculations) is necessarily an epistemic uncertainty.

It is often said that chaos enables free will to exist in a completely deterministic universe. Predictability (determinism) exists in chaotic systems only in the short-term, because of the rapid divergence within the system; in the long-term any divergence creates an inability to calculate what will happen (ergo, stochasticism). The universe may indeed be completely deterministic, but there are "calculation barriers" that make long-term deterministic measurement a real problem.

"Determinism" is an algorithm that examines a signal and tells how predictable things are in the short-term. If the measure is near 0, then the average predictability of a point In phase space from its previous location is poor, as would occur with random noise; if the measure is near 1, then the predictability is high, as would occur for example with sine-wave data. If the data are nonstationary, then the accumulated algorithmic predictability cannot be accurately determined. Most known deterministic measures are unable to quantify, on a data-point by data-point basis, what is happening in time to the output of the system (i.e. generator) if the data are nonstationary. Only the present PD2i, which treats the problem of data nonstationary can do this in a highly accurate manner.

Deterministic measures are inherently more accurate than a comparable stochastic one if there is some short-term structure in the data and the data are stationary. Thus, if the data are stationary, mean PD2i can tell you something about a change in the state of the generator of the signal that the stochastic mean of the data cannot. This is also true regarding the standard deviation, power spectrum or any other stochastic measure used on the same data.

This greater sensitivity, presumably of the short-term variation, has been shown to be useful in detecting changes in biological data that the stochastic measures cannot make. For example, analysis of the RR intervals of the electrocardiogram of a group of pigs undergoing experimental myocardial infarction showed significant differences in mean PD2i before and after occlusion, whereas neither the RR mean nor the RR power spectrum were able to detect such differences. These same results were found when comparing RR intervals from human patients who manifested fatal ventricular fibrillation that day and matched controls who only manifested non-fatal ventricular tachycardia during the next 3 years. This greater sensitivity leads to greater individual specificity and the latter is the main reason why chaos theory has important implications for biology and medicine.

This disclosure teaches that a fundamental difference in sensitivity of measurement occurs when one posits that the variation in the data is caused, as opposed to being random. Even without a perfect way to define what chaos is, or how to determine whether or not it is in the data, one still finds that the determinism-based measures are sensitive to changes in the generator of the data that the stochastic measures cannot probe.

Figure 1:
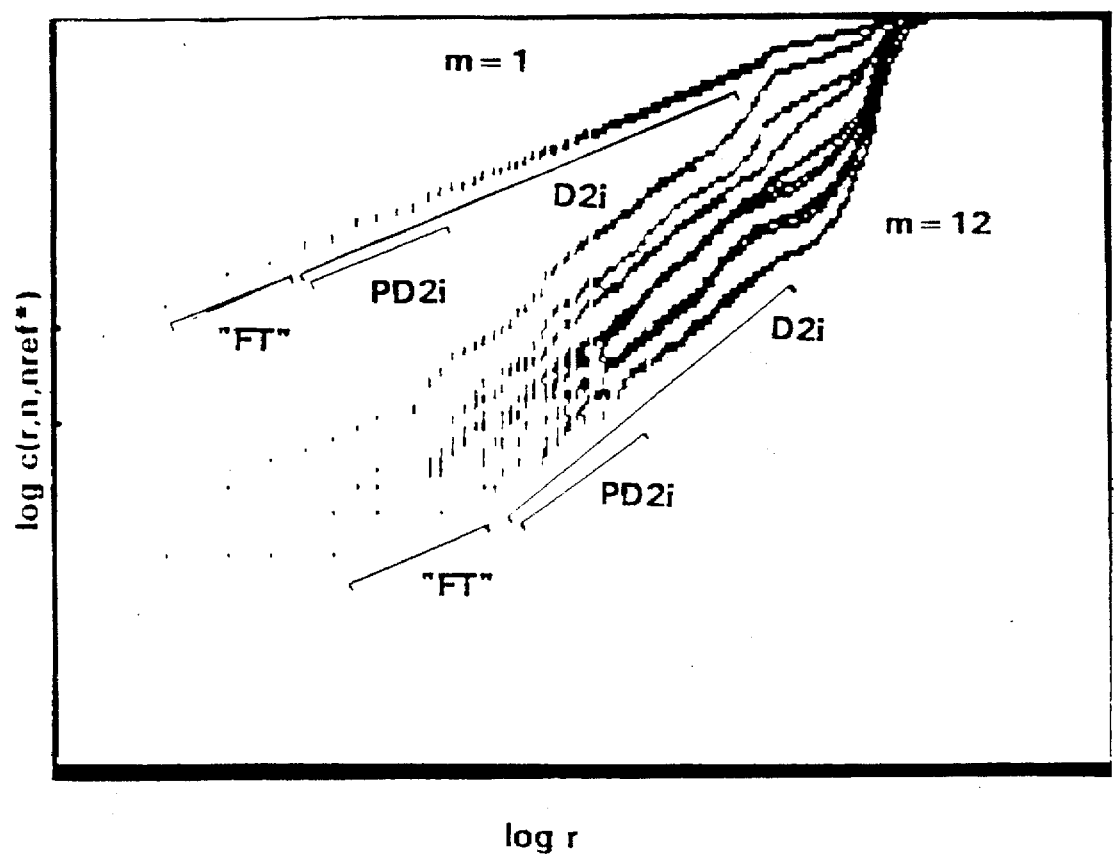
FIG. 1 plots log $C(r,n,nref\star)$ versus log r in accordance with the concepts of present invention.

FIG. 1 plots log $C(r,n,nref\star)$ versus log r and depicts the crucial idea behind the PD2i algorithm. It is only the smallest initial part of the linear scaling region that should be considered if data nonstationarities exist. In this case the data were made by concatenating 1200 point data subepochs from a sine wave, Lorenze data, a sine wave, Henon data, a sine wave, and random noise. The reference vector was in the Lorenz subepoch. For the correlation integral where the embedding dimension m=1, the segment for the floppy tail ("FT") is avoided by a linearity criterion of LC=0.30; the linear scaling region for the entire interval (D2i) is determined by plot length PL=1.00, convergence criterion CC=0.40 and minimum scaling MS=10 points. The species specific scaling region where the i- and j-vectors are both in the Lorenz data (PD2i) is set by changing plot length to PL=0.15 or lower. Note that at the higher embedding dimensions (e.g. m=12) after convergence of slope vs embedding dimension has occurred, the slope for the PD2i segment is different from that of D2i. This is because the upper part of the D2i segment (D2i–PD2i) is contaminated by nonstationary i–j vector differences where the j-vector is in a nonstationary species of data with respect to the species the i-vector is in.

Figure 2:
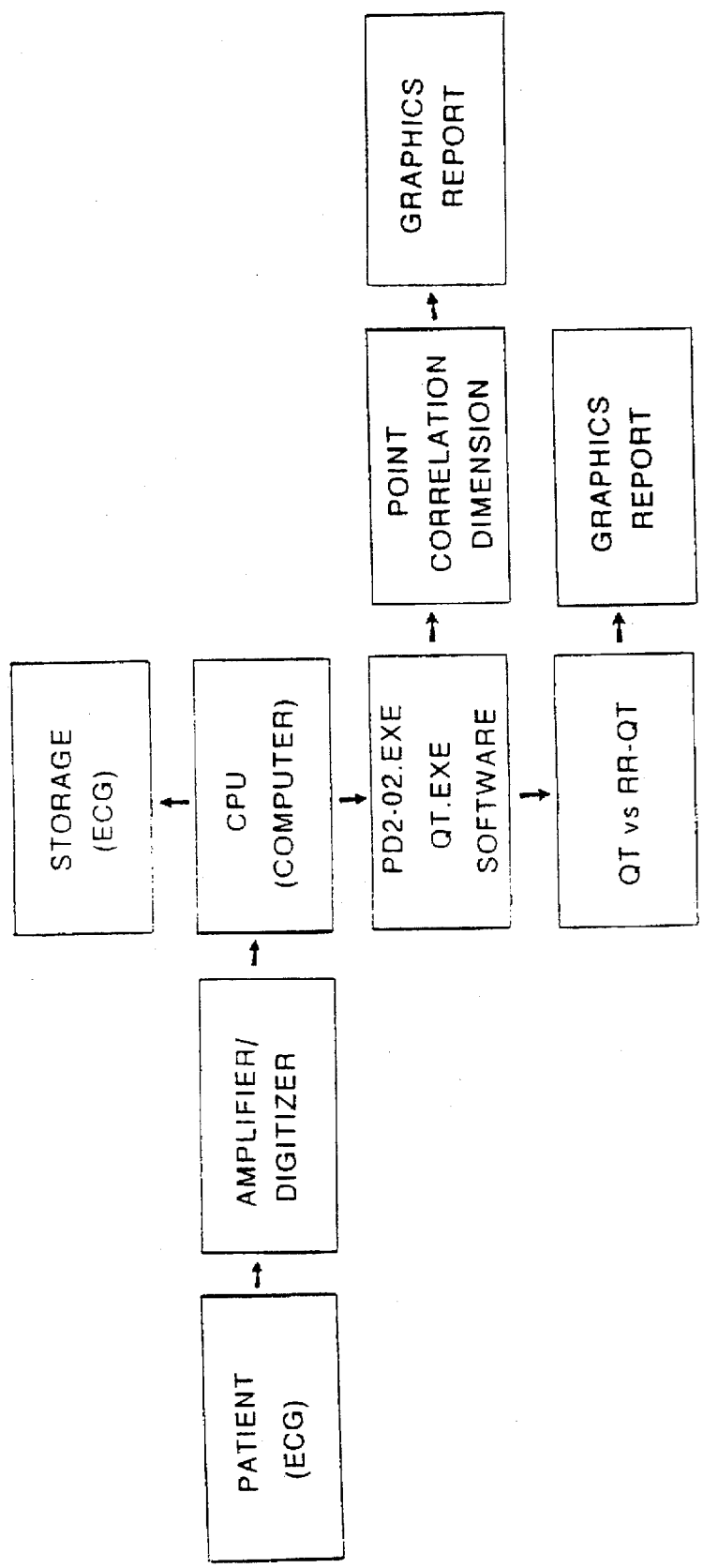
FIG. 2 is a flow diagram for the logic of the algorithm in accordance with the present invention applied to the ECG in cardiology.

FIG. 2 shows a flow diagram of the invention applied to a cardiac patient or a normal subject undergoing cardiac evaluation. Electrocardiographic data (ECG) from the subject is made by a conventional amplifier, digitized, and then given as input to a computer for analysis. First RR and QT intervals are made from the ECG data; then they are analyzed by the PD2i software (PD2-02.EXE) and QTvsRR-QT software (QT.EXE). The Point Correlation Dimension is then calculated as a function of time and displayed; the QT vs RR-QT plot is also made and displayed. Graphics Reports are then made for assessing risk. The digitized ECG is offloaded for storage.

Figure 3:
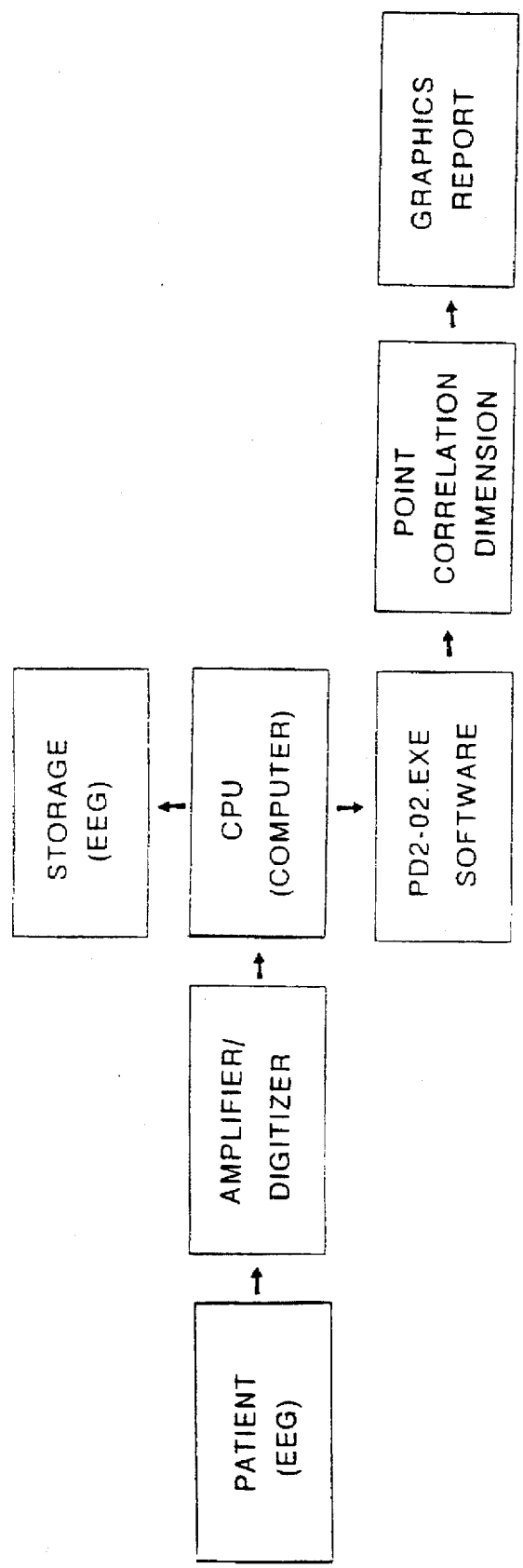
FIG. 3 is a flow diagram for the logic of the algorithm in accordance with the present invention applied to the EEG and related concepts in neurophysiology.

FIG. 3 shows the invention applied to an epilepsy patient or normal subject undergoing neural analysis. Electroencephalographic data (EEG) from the subject is made by a conventional amplifier, digitized, and then given as input to a computer for analysis. The Point Correlation Dimension is then calculated as a function of time by the PD2i software (PD2-02.EXE) and displayed. A Graphics Report is then made for assessing location of epileptic focii and/or alteration of cognitive state.

Other similar applications of the invention are possible. The source of the electrophysiological signal will be different, and the structure of the graphics report(s) will be specific to the medical and/or physiological objectives. All analyses will use the PD2i algorithm, in some software form, and may be accompanied by other confirmatory analyses.

An electrophysiological signal is amplified (gain of 1,000) digitized (1,000 Hz) and then analyzed by the PD2i, a deterministic dimensional algorithm that is insensitive to data nonstationarities and can be used on data that have both linear and nonlinear structures. Once the signal is digitized, it may be further reduced (e.g. conversion of ECG data to RR interval data) prior to processing. Analysis of RR interval data has been repeatedly found to enable risk-prediction between large groups of subjects with different pathological outcomes (e.g. ventricular fibrillation "VF" or ventricular tachycardia "VT"). In a study (see examples below) using sampled RR data from high risk patients, it was found that PD2i could discriminate those that later went into VF from those that did not.

Several nonproprietary algorithms were also used as comparative studies on physiological data. None of these algorithms could discriminate risks that the PD2i is capable of making. In the electrocardiographic analyzer apparatus contemplated in the present invention, the QT subinterval of each RR interval will be made by the QT.EXE software described herein. The calculation of the QT interval enables a joint plot of the QT vs RR-QT subintervals, which can predict risk of fatal arrhythmias such as VF in high-risk patients all of whom exhibit ventricular VT, when the dynamics enter a previously defined exclusion area for that patient. The rationale for this prediction is based on a theory linking the subintervals to mathematical models as presented below in Example 4.

The method and apparatus used to examine entry of the joint subinterval dymanics into the exclusion area for predicting risk of dynamical arrhythmogenesis in both cardiac patients and normal subjects is one embodiment of the present invention. Once the PD2i and QTvsRR-QT values are calculated, as a function of time, they can be presented in a variety of graphics modes that will summarize the current results and provide a clinically useful predictor. These graphic reports provide visualization of the outputs of the PD2i and QTvsRR-QT algorithms.

EXAMPLE 1

The PD2i algorithm has been applied to RR intervals of the electrocardiograms of 60 cardiac patients in a blinded, controlled, retrospective study, and PD2i's<1.2 were found to discriminate risk of imminent fatal arrhythmias (i.e. the onset of ventricular fibrillation, VF, within 24-hrs), among high-risk control subjects (i.e. patients with documented ventricular tachycardia, VT, who lived for more than 3 years and had PD2i's<1.2; sensitivty=100%, specificity=86%, p<0.01). Tables 2, 3 and 4, below, shows the composite data in human cardiac patients.

TABLE 2

Point-D2 and Clinical Data: the minimum Point-D2 (Min PD2) of the heartbeat intervals (R—R; A, B, C samples, 24-h Holter-tapes, 512 Hz A/D) discriminates among patients with nonsustained ventricular tachycardia those who will manifest ventricular fibrillation (VF) from those who will not (NS-VT).

AMBULATORY NONSYMPTOMATIC PATIENTS

| Pt[1] | TF/NP[2] | Clin Diag Arr[3] | With PVCs Min PD2[4] | Edit PVCs Min PD2[5] | Excurs PD2 < 1.2[6] | | | R—R SDs[7] | | | Holter-Tape[8] | | |
|---|---|---|---|---|---|---|---|---|---|---|---|---|---|
| | | | | | A | B | C | A | B | C | TL | VF | Hosp |
| 1 | TP | VF | 1.2 | nc | 01 | 01 | 11 | 19 | 16 | 16 | 8 | 21:00 | I |
| 2 | TP | VF | 1.1 | nc | 11 | 11 | 01 | 6 | 18 | 15 | 9 | 21:00 | I |
| 3 | TP | VF | 1.0 | 1.1 | 11 | 11 | 11 | 25 | 14 | 18 | 21 | 07:30 | I |
| 4 | TP | VF | 0.7 | nc | 01 | 01 | 11 | 7 | 7 | 5 | 24 | 06:30 | I |
| 5 | | VF | 0.5n | nc | NA | 1 | 11 | 134 | 133 | 018 | 18 | 10:00 | O |
| 6 | TP | VF | 0.4 | 0.5 | 11 | 11 | 1 | 4 | 5 | 69 | 24 | 09:30 | I |
| 7 | TP | VF | 0.5 | 0.6 | 11 | 11 | 11 | 9 | 10 | 24 | 4 | 15:45 | I |
| 8 | | VF | 0.9n | NA | 11 | 11 | 11 | 33 | 37 | 21 | 3 | 14:00 | I |
| 9 | TP | VF | 1.0 | nc | 11 | 01 | 11 | 6 | 18 | 6 | 14 | 11:00 | I |
| 10 | | VF | 0.9n | NA | 11 | 11 | 11 | 10 | 14 | NA | 9 | 19:45 | I |
| 11 | TN | NS-VT | 1.4 | 1.6 | 00 | 00 | 00 | 25 | 24 | 26 | 23 | | I |
| 12 | TN | NS-VT | 1.5 | nc | 00 | 00 | 00 | 15 | 14 | 12 | 24 | | I |
| 13 | TN | PVC | 1.5 | nc | 00 | 00 | 00 | 14 | 18 | 22 | 24 | | O |
| 14 | TN | NS-VT | 1.6 | nc | 00 | 00 | 00 | 17 | 28 | 14 | 24 | | O |
| 15 | TN | NS-VT | 1.9 | nc | 00 | 00 | 00 | 32 | 17 | 23 | 23 | | I |
| 16 | TN | NS-VT | 1.6 | nc | 00 | 00 | 00 | 28 | 44 | 54 | 24 | | O |
| 17 | TN | NS-VT | 1.5 | nc | 00 | 00 | 00 | 37 | 38 | 38 | 24 | | I |
| 18 | TN | NS-VT | 1.4 | nc | 00 | 00 | 00 | 85 | 7 | 17 | 24 | | I |
| 19 | TN | NS-VT | 1.4 | nc | 00 | 00 | 00 | 7 | 14 | 9 | 23 | | I |
| 20 | TN | NS-VT | 2.2 | nc | 00 | 00 | 00 | 21 | 24 | 26 | 24 | | I |
| 21 | | NS-VT | 1.3n | NA | 00 | 00 | 00 | 37 | 74 | NA | 24 | | I |
| 22 | TN | PVC | 1. | NA | 00 | 00 | 00 | 14 | 17 | 18 | 24 | | O |
| 23 | TN | PVC | 1.4 | 1.5 | 00 | 00 | 00 | 11 | 13 | 14 | 24 | | O |
| 24 | TN | PVC | 1.3 | NA | 00 | 00 | 00 | 15 | 19 | 16 | 24 | | O |
| 25 | | PVC | 1.8n | NA | 00 | 00 | 00 | 19 | 50 | 63 | 24 | | O |
| 26 | TN | PVC | 3.0 | nc | 00 | 00 | 00 | 18 | 22 | 19 | 21 | | O |
| 27 | | PVC | 1.6n | NA | 00 | 00 | 00 | 100 | 41 | 57 | 24 | | O |
| 28 | TN | PVC | 1.3 | NA | 00 | 00 | 00 | 20 | 15 | 20 | 24 | | O |
| 29 | TN | PVC | 1.4 | 1.5 | 00 | 00 | 00 | 24 | 22 | 15 | 24 | | O |
| 30 | TN | PVC | 1.4 | NA | 00 | 00 | 00 | 24 | 16 | 14 | 20 | | O |

TABLE 2-continued

Point-D2 and Clinical Data: the minimum Point-D2 (Min PD2) of the heartbeat intervals (R—R; A, B, C samples, 24-h Holter-tapes, 512 Hz A/D) discriminates among patients with nonsustained ventricular tachycardia those who will manifest ventricular fibrillation (VF) from those who will not (NS-VT).

AMBULATORY NONSYMPTOMATIC PATIENTS

| Pt[1] | TF/NP[2] | Clin Diag Arr[3] | With PVCs Min PD2[4] | Edit PVCs Min PD2[5] | Excurs PD2 < 1.2[6] | | | R—R SDs[7] | | | Holter-Tape[8] | | |
|---|---|---|---|---|---|---|---|---|---|---|---|---|---|
| | | | | | A | B | C | A | B | C | TL | VF | Hosp |
| 31 | TN | PVC | 1.6 | nc | 00 | 00 | 00 | 24 | 16 | 21 | 24 | | O |
| 32 | TN | PVC | 2.0 | NA | 00 | 00 | 00 | 23 | 26 | 23 | 24 | | I |
| 33 | TN | PVC | 1.6 | nc | 00 | 00 | 00 | 40 | 19 | 32 | 24 | | O |
| 34 | FP | NS-VT | 0.4 | nc | 11 | 1— | 11 | 6 | 7 | 4 | 11 | | I |
| 35 | FP | NS-VT | 0.5 | 0.6 | 11 | 11 | 11 | 15 | 17 | 10 | 24 | | O |
| 36 | FP | NS-VT | 0.6 | 0.5 | 11 | 10 | 11 | 7 | 9 | 6 | 24 | | I |
| 37 | FP | NS-VT | 0.8 | nc | 11 | 11 | 11 | 7 | 11 | | 14 | | I |
| 38 | | VF | 3.3n | NA | NA | NA | NA | 133 | 131 | 124 | 2 | 10:40 | I |
| 39 | TP | VF* | 0.6 | | 0 | 1 | 1 | 17 | 4 | 14 | | | |
| 40 | TP | VF* | 0.6 | | 1 | 1 | 1 | 29 | 6 | 15 | | | |
| 41 | TP | VF* | 0.6 | | 1 | 1 | 1 | 4 | 8 | 5 | | | |
| 42 | | VF | 4.2n | | 0 | 0 | 0 | 54 | 45 | 44 | | | |
| 43 | TP | VF* | 0.7 | | 0 | 1 | 0 | 30 | 33 | 41 | | | |
| 44 | | VF | 1.9n | | 0 | 0 | 0 | — | — | — | | | |
| 45 | | VF | 1.2n | | 1 | 0 | 0 | — | — | — | | | |
| 46 | TP | VF* | 0.5 | | 1 | 1 | 1 | 10 | 10 | 6 | | | |
| 47 | TP | VF* | 0.6 | | 1 | 1 | 1 | 9 | 4 | — | | | |
| 48 | | VF | 0.5n | | 1 | 1 | 0 | 78 | 15 | — | | | |
| 49 | TP | VF* | 0.7 | | 0 | 1 | 1 | 19 | 15 | 11 | | | |
| 50 | TP | VF* | 0.5 | | 1 | 1 | 1 | 3 | 6 | 7 | | | |
| 51 | TP | VF* | 0.6 | | 1 | 1 | 1 | 16 | 62 | 20 | | | |
| 52 | TP | VF* | 0.6 | | 1 | 1 | 1 | 23 | 49 | 7 | | | |
| 53 | TP | VF* | 0.5 | | 1 | 1 | 1 | 6 | 6 | 8 | | | |
| 54 | | VF | 0.8n | | 1 | 1 | 1 | 72 | — | 99 | | | |
| 55 | TP | VF* | 0.5 | | 1 | 1 | 1 | 9 | 3 | — | | | |
| 56 | TP | VF* | 0.8 | | 1 | 1 | 0 | 8 | 19 | 53 | | | |
| 57 | TP | VF* | 0.5 | | 1 | 1 | 1 | 6 | 5 | 9 | | | |
| 58 | | VF | 0.6n | | 1 | 1 | 1 | 37 | 4 | 13 | | | |
| 59 | | VF | 6.6n | | 0 | 0 | 0 | — | — | — | | | |
| 60 | TP | VF* | 0.6 | | 0 | 1 | 0 | 13 | 7 | 17 | | | |
| 61 | TP | VF* | 0.6 | | 1 | 1 | 1 | 30 | 5 | — | | | |

Note:
Specificity of PD2i < 1.2 predicting VF outcome (Patients 1–61) = 86%. Sensitivity for PD2i < 1.2 predicting VF outcome (Patients 1–61) = 100% ($p < .001$).

Table 2, End Notes

[1] Patient number: Pts 1–21 (1st study, blinded) Pts 22–38 (2nd study, double-blinded); for Pts 39–61 (3rd study, blinded); for Pts 62–80 (4th study, double-blinded); (15 min, prior to inducibility testing).

[2] T = true, F = false, N = negative, P = positive, where true = VF and positive = PD2 < 1.2; omitted entry means PS2 could not be calculated.

[3] Clin Diag Arr = clinically diagnosed arrhythmias; VF = nonsustained ventricular tachycardia ending in ventricular fibrillation; NS-VT = nonstained ventricular tachycardia; PVC = premature ventricular complexes; NORM = normal.

[4] MinPD2 = minimum point correlation-dimension (in dimensions, n = probably not a valid estimate because more than 75% of estimates rejected); ARRHYTHMIAS AND ARTIFACTS NOT REMOVED from the R—R data; PD2 software from Neurotech Laboratories, Inc., 399 Autumn Drive, Bangor, PA.

[5] Same as above, but artifacts and arrhythmias removed by digital overwritting with 5-point copies from neighborhood; nc = no change; NA = not available/applicable.

[6] Excurs PD2 < 1.2 = excursions of PD2 < 1.2; 1 = at least one excursion occurred during the 6.5 min epoch; 0 = no excursion occurred; two adjacent 6.5 min epochs comprise one A, B or C epoch; A = initial epoch, B = mid epoch, C = final epoch.

[7] R—R SD = standard deviation of R—R intervals (msec) during a 2 to 3 min stationary period without arrhythmias or artifacts; A = initial epoch, B = mid epoch, C = final epoch. VF, NS-VT, PVC not significantly different ($F = 1.6$, $df = 109$).

[8] Holter Tape; TL = tape length in hours; VF = time of occurrence of VF; Hosp = hospital inpatient (I) or outpatient (O).

*Statistics: VF versus NSVT + PVC significantly different (MinPD2, $P < .001$, $F = 9.4$, $df = 36$, Pts 1–38); NSVT vs PVC not significantly different; S + VF vs S + VT not significantly different (Pts 62–80); S + VF vs NSVT and S + VT vs NSVT significantly different ($P < .01$); One-way Analysis of Variance, with multiple-tests alpha-protection; True Epistat software, Epistat Services, Richardson, TX. Logistic Regression Model (no VF vs VF, Pts 1–38) show MinPD2 ($P < .001$), Ej-Fr (P = not significant), MinPD2 and Ej-Fr ($P < .002$); software from Stata Computing Resource Center, Los Angeles, CA.

TABLE 3

SYMPTOMATIC PATIENTS, OFF DRUGS

| Pt[1] | Clin Diag TF/NP[2] | Arr[3] | With PVCs Min PD2[4] | Edit PVCs Min PD2[5] | Excurs PD2 < 1.2[6] A | B | C | R—R SDs[7] A | B | C | Holter-Tape[8] TL | VF | Hosp |
|---|---|---|---|---|---|---|---|---|---|---|---|---|---|
| 62 | (TP) | S + VF* | 0.4 | | Table 3 LEGEND | | | | | | | | |
| 63 | | S + VF | —n | | S = previously documented syncope | | | | | | | | |
| 64 | | S + VF | —n | | VF = previously documented VF-converted | | | | | | | | |
| 65 | (TP) | S + VF* | 0.5 | | VT = previously documented VT | | | | | | | | |
| 66 | (FP) | S + VF* | 1.1 | | TP = true positive predicting prev. VF | | | | | | | | |
| 67 | (FP) | S + VF* | 0.6 | | FP = false positive predicting prev. VT | | | | | | | | |
| 68 | (FP) | S + VF* | 0.5 | | NOTE: only 10 of 19 had ectopy rates | | | | | | | | |
| 69 | (FP) | S + VF* | 1.0 | | low enough to enable valid PD2i calcu- | | | | | | | | |
| 70 | | S + VF | 1.7n | | lation; PD2i < 1.2 predicts symptomatic | | | | | | | | |
| 71 | (TN) | S + VF* | 1.4 | | condition in 9 of 10 VF/VT patients | | | | | | | | |
| 72 | (FP) | S + VF* | 0.6 | | | | | | | | | | |
| 73 | (FP) | S + VF* | 0.4 | | | | | | | | | | |
| 74 | | S + VF | 2.4n | | | | | | | | | | |
| 75 | | S + VF | 1.1n | | | | | | | | | | |
| 76 | | S + VF | 1.2n | | | | | | | | | | |
| 77 | | S + VF | 1.3n | | | | | | | | | | |
| 78 | | S + VF | 3.0n | | | | | | | | | | |
| 79 | | S + VF | 2.8n | | | | | | | | | | |
| 80 | (FP) | S + VF* | 0.8 | | | | | | | | | | |

NORMAL CONTROLS

| Pt | TF/NP | Arr | PD2 | PD2 | A | B | C | A | B | C | TL | VF | Hosp |
|---|---|---|---|---|---|---|---|---|---|---|---|---|---|
| 1 | TN | NORM | 1.8 | — | 0 | 0 | 0 | 86 | 94 | 80 | — | — | 33 M |
| 12 | TN | NORM | 1.7 | — | 0 | 0 | 0 | 86 | 98 | 84 | — | — | 25 M |
| 25 | TN | NORM | 1.6 | — | 0 | 0 | 0 | 71 | 55 | 56 | — | — | 50 M |

Table 3, End Notes:
see end notes for Table 2, page 38, supra.

TABLE 4

| Pt[1] | Ej Fr[9] | PVC/ Hr[10] | A[11] | S[12] | Meds[13] | Coronary Anatomy[14] | History[15] MI | AN | HF | HT | DM |
|---|---|---|---|---|---|---|---|---|---|---|---|
| 1 | NA | 84 | 65 | M | P | NA | + | + | − | − | − |
| 2 | 28 | 33 | 56 | M | DHSF | 50% LM | + | + | + | − | − |
| 3 | 50 | 10 | 52 | F | VN | Min | + | + | − | − | − |
| 4 | 60 | 80 | 61 | F | DHe | Min | not applicable | | | | |
| 5 | 32 | 270 | 73 | M | PPrDF | 60% RC | − | − | + | − | + |
| 6 | 33 | 407 | 63 | F | NDVF | Min | − | + | + | − | − |
| 7 | 60 | 900 | 42 | M | DCoF | Min | + | − | − | − | + |
| 8 | 35 | 506 | 57 | M | DiN | NA | + | + | − | − | − |
| 9 | NA | 105 | 80 | M | NDQ | NA | − | + | − | − | − |
| 10 | NA | 200 | 79 | M | FD | 70% LAD, 30% LM, 30% RC | + | − | + | + | − |
| 11 | 67 | 114 | 58 | M | Mp | 50% RC | + | − | − | + | − |
| 12 | 50 | 188 | 63 | M | DiNHe | 99% RC | + | + | − | + | − |
| 13 | 61 | 2 | 57 | M | DiN | NA | not applicable | | | | |
| 14 | NA | 61 | NA | M | NfDDiFE | NA | not applicable | | | | |
| 15 | 25 | 45 | 53 | M | DDi | TVD | 30 | + | + | − | − |
| 16 | 87 | 1 | 53 | F | Di | NA | not applicable | | | | |
| 17 | 50 | 2 | 66 | M | QD | 100% RC, 50% LM, 70% CX | − | + | − | − | + |
| 18 | 50 | 29 | 68 | M | QPNfD | 100% RC, 100% LAD | − | + | − | − | − |
| 19 | 32 | 108 | 63 | M | NCNfD | 99% LAD, 99% CX | − | + | − | + | − |
| 20 | 14 | 1152 | 59 | M | NfD | NA | + | + | − | + | − |
| 21 | NA | 984 | 50 | M | QNNf | NA | − | + | − | − | − |
| 22 | 28 | 229 | 64 | M | DiDN | NA | + | + | − | + | + |
| 23 | 37 | 13 | 68 | M | DiNP | NA | + | + | − | + | − |
| 24 | 30 | 72 | 49 | M | NNfP | NA | + | + | − | + | − |
| 25 | 32 | 24 | 51 | M | NfMpDN | 95% LAD, 95% RC | + | + | + | + | − |
| 26 | 32 | 11 | 57 | F | NFDi | NA | + | − | − | − | − |
| 27 | 21 | 12 | 59 | F | MpCN | NA | + | − | − | + | − |
| 28 | 23 | 77 | 64 | M | DiNFC | NA | + | + | − | − | − |
| 29 | 39 | 7 | 55 | M | NfMp | NA | + | + | − | − | − |
| 30 | 25 | 1173 | 61 | M | CDNfN | NA | + | + | − | + | − |
| 31 | 32 | 6 | 72 | M | NDi | NA | + | + | − | + | − |
| 32 | 64 | 15 | 67 | M | NDDi | 75% RC, 95% LAD | + | + | − | + | + |
| 33 | 22 | 6 | 53 | M | CDN | NA | + | − | + | + | − |
| 34 | NA | 3 | 47 | M | DiMp | 80% LAD, 80% RC | + | − | − | + | − |
| 35 | 20 | 360 | 63 | M | DN | NA | not applicable | | | | |

TABLE 4-continued

| | | | | | | | | | | | |
|---|---|---|---|---|---|---|---|---|---|---|---|
| 36 | 29 | 60 | 64 | M | PcMxDi | 100% LM, 100% RCA, OpGrRCA | – | + | – | + | – |
| 37 | 29 | 12 | 62 | M | AtDi | 90% LAD, 90% RC | – | + | – | + | – |
| 38 | 14 | 86 | 55 | M | EDB | NA | + | + | + | + | + |
| 39–80 | | records NA | | | | | | | | | |
| 101 | NA | NA | 33 | M | NA | NA | | | NA | | |
| 112 | NA | NA | 25 | M | NA | NA | | | NA | | |
| 125 | NA | NA | 50 | M | NA | NA | | | NA | | |
| Pt[1] | | Comments[16] | | | | | | | | | |

1 type II aortic aneurysm
2 heart failure
3–5 days after back surgery
4 evaluation of ventricular arrhythmias; resuscitated in hospital
5 evaluation of ventricular arrhythmias
6 heart failure
7 1 day after mitral commisurotomy, resuscitated in hospital
8 10 days after non-Q infarction
9 4 days after exploratory laparotomy
10 meningeoma; autopsy consistent with ant. lat. ischemia; old septal infarct
11 3 weeks after MI
12 post-MI stratification
13 NA
14 NA
15 coronary artery bypass graft
16 NA
17 coronary artery bypass graft, pre work up
18 coronary artery bypass graft, pre work up
19 NA
20 weeks post-MI; a single VT-triplet was observed
21 coronary artery bypass graft, post 10 days, work up for palpitations
22 5 days after MI
23 5 days after MI
24 1 week after MI
25 3 months after MI
26 2 weeks after MI
27 5 weeks after MI
28 2 weeks after MI
29 10 months after MI
30 5 days after MI
31 1 week after MI
32 1 week after unstable angina
33 1 month after MI
34 6 weeks after MI
35 NA
36 work up for angina
37 coronary artery bypass graft, pre work up
38 post-MI stratification
Table 4, End Notes:
for end notes [1–8] for Table 4, see end notes for Table 2, page 38, supra.
[9]EJ Fr = ejection fraction (in percent); VF, NS-VT, PVC not significantly different ($F = 0.48$, $df = 31$).
[10]PVC/Hr = premature ventricular complexes per hour, averaged over the full length of the Holter-monitored electrocardiogram (Marquette, Inc.); VF, NS-VT and PVC not significantly different ($F = 0.45$, $df = 37$).
[11]age
[12]Gender M = male (81%), F = female (19%), B = black (23%), W = white (66%), H = Hispanic (5%), A = Asian (5%).
[13]Medications at time Holter tape made; Pts 39–61 had no medical records available; Pts 62–80 were off medication, for more than 7 half-lives of drug, prior to cardiac electrophysiology assessment of VT-inducibility; for normals, na = not applicable, no statistically significant drug-effects are detectable for this number of subjects. Abbreviations: At = Atenolol, B = Bumetanide, C = Captopril, Co = Coumadin, D = Digoxin, Di = Diltiazem, E = Enduronyl, F = Furosamide, H = Hydralazine, He = Hetz, Mp = Metroprolol, Mx = Mexilitine, N = Nitrates, Nf = Nifedipine, P = propranolol, Pc = Procainamide, Pr = Prazosin, Q = Quinidine, S = Spirono-lactone, V = Vasopresin.
[14]Coronary Anatomy; percentage occlusion on coronary angiography; RC = right coronary; LM = left main; LAD = left anterior descending; CX = circumflex; TVD = triple vessel disease; OpGrRC = open graft to right circumflex; Min = minimal coronary disease.
[15]History = medical history; MI = myocardial infarction; AN = angina; HF = heart failure; HT = hypertension; DM = diabetes mellitus.
[16]Comments written on medical records.

Additional preliminary data show that the separation in time of the recording and prediction and the actual time-of-occurrence of VF can be as much as 42 days and still exhibit high sensitivity and specificity. Table 5, below, shows these data.

TABLE 5

Blinded 24-hour study of the Point-D2 (PD2i) of the heartbeats in patients from the Cardiac Arrhythmia Pilot Study.[1] The R—R intervals were made at a resolution of 128-Hz for the digitizing rate of the ECG.[2]

| | Prediction by PD2i[3] | Actual Event[4] | Days Separating Predition from Event | Type of Outcome[5] |
|---|---|---|---|---|
| NOTE: | − | lived | >1000 | TN |
| half of the | − | lived | >881 | TN |
| FP's may be | − | died | 336 | RFN |
| due to a | + | died | 231 | RTP |
| low digitizat- | − | died | 149 | RFN |
| ion rate for | + | died | 42 | RTP |
| the ECG | + | died | 37 | TP |
| | + | died | 9 | TP |
| | + | died | 7 | TP |
| | +* | died | 1 | TP |
| | +* | died | 1 | TP |
| | +* | died | 1 | TP |
| | +* | died | 1 | TP |
| | +* | died | 1 | TP |
| | +* | died | 1 | TP |
| | +* | died | 1 | TP |
| | + | lived | >1086 | FP |
| | + | lived | >1062 | FP |
| | + | lived | >904 | FP |
| | + | lived | >1020 | FP |
| | ++* | lived | >1000 | FP |
| | ++* | lived | >1000 | FP |
| | +−# | lived | >1000 | TN |
| | +−# | lived | >1000 | TN |

Table 5, End Notes
[1] R—R interval files made with Marquette scanner by Thomas Bigger (Columbia University, New York).
[2] Only 24 of 51 files could be examined because of low 128-Hz resolution.
[3] + = minPD2 < 1.2; − = minPD2 > 1.2; * = same result obtained using 512-Hz digitizing rate for the ECG; # = opposite result obtained using 512-Hz digitizing rate.
[4] VF was cause of death.
[5] Predicted outcome: TN = true negative; TP = true positive; FP = false positive; FN = false negative; RFN = critical-range false negative; RTP = critical-range true positive (i.e., this range exhibits prediction divergence and is the probable limit of the interval over which PD2-prediction can be expected to work).

EXAMPLE 2

Not only is the PD2i useful in analyzing physiological time series data such as the electrocardiogram (e.g. RR intervals made from the ECG), but it is also capable of analyzing the electroencephalogram (EEG). It has been applied to simultaneously-recorded scalp-EEG's and electrocorticography-EEG's obtained from 5 patients will epilepsy. It was found that the scalp electrodes nearest the suprapial cortical electrodes that were the earliest to show paroxysmal activity during an epileptic seizure (i.e. the leads that by the electrocorticography method locate the epileptic focus) had a statistically significantly larger PD2i variance (standard deviation) than any of the other scalp leads including the perifocal ones. These data are shown in FIG. 5.

Figure 5:
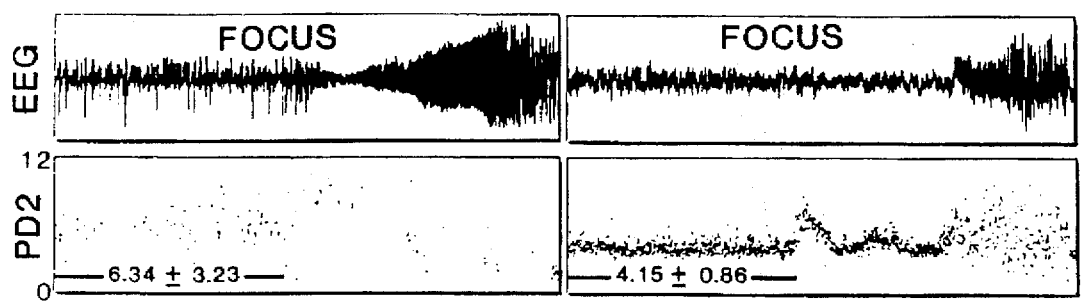
FIG. 5 shows PD2i of EEG's recorded simultaneously from the pia (PIA) and scalp (SCALP) in a conscious human with documented epilepsy.
Figure 5:
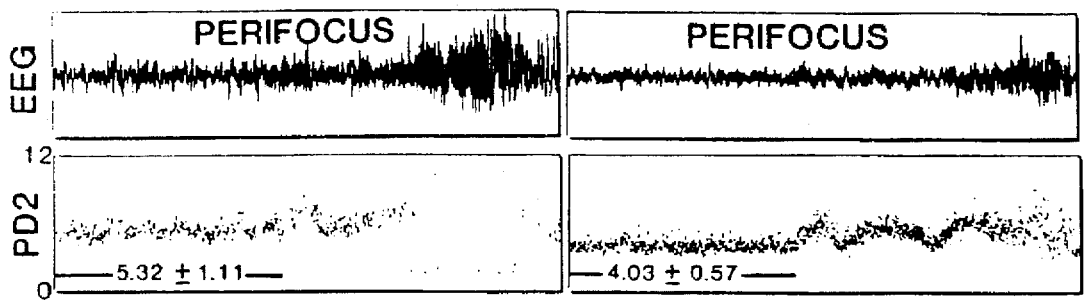

FIG. 5 shows PD2i of EEGs recorded simultaneously from the pia (PIA) and scalp (SCALP) in a conscious human with documented epilepsy. Recordings were made from the surface of the cortex with electrocorticography electrodes and from the scalp with conventional scalp electrodes. Data were recorded from two sites one minute before a seizure, (1) above the epileptic focus as defined by the electrocorticography lead that showed the earliest high frequency activity prior to the seizure, and (2) 2-cm away from the focus; the scalp leads were placed immediately above the selected electrocorticography leads. The mean PD2i and its standard deviation are shown for each of the preseizure epochs indicated.

EXAMPLE 3

Analysis of the EEG's from both animals (cats) and humans show evoked alterations in the baseline PD2i of the EEG that persists in time between a memory storage event and a memory recall event. For example, when a group of 10 humans were instructed that a shock would be "strong," the resulting PD2i of the baseline EEG was reduced compared to the condition in which each of the same subjects was instructed that a shock of the same physical intensity would be "weak."

Thus, from the time of the instruction onward the baseline PD2i maintained an altered value. As the shocks were of the same intensity, the evoked EEG potentials were of the same amplitude, for all components, but an altered PD2i of the same event-related potentials showed statistically significantly different components. Thus, the results from the transient PD2i responses confirmed those of the tonic baseline-effects. A similar baseline EEG alteration was noted in 4 cats undergoing classical conditioning to a tone. The baseline PD2i was reduced during shock reinforcement of the tone, that is, as compared to the condition in which the tone was presented without reinforcement. Thus, the PD2i of the EEG provides electrophysiological evidence of a persistent "engram" which bridges the time gap between the presentation of a learned stimulus and its later recall. The data from the above described human study are shown in FIG. 6.

Figure 6:
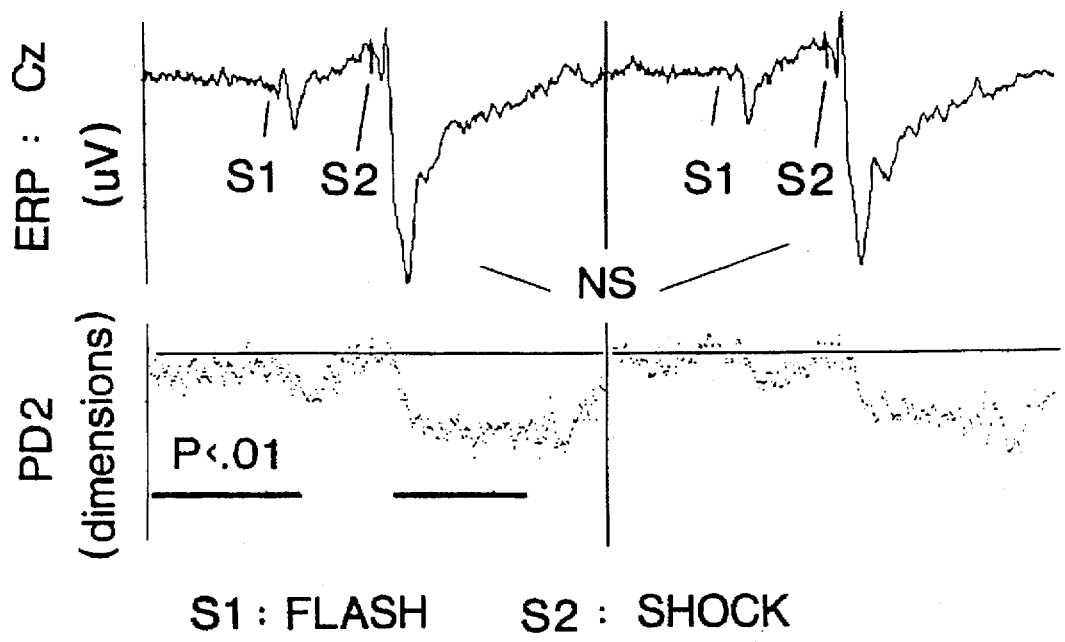
FIG. 6 depicts data from a human study in conjunction with the present invention.

FIG. 6 shows the effects of insrtuctional set (expectancy) on the event-related potential (ERP) and the PD2i of the same potentials. The data are computer averages of 10 trials in 10 human subjects for two sessions in which a warning stimulus (S1, a moderate intensity flash) preceded by 0.5 sec the occurrence of a moderate intensity skin shock (S2). The subject had been instructed prior to each session to expect either a "weak" or a "strong" shock; the S2's were equal in intensity and previously judged by the subject to be "moderate". There were no effects of instructional set on the ERP components (NS), but the PD2i's showed a statistically significantly lower baseline for the expect "strong" shock condition and a significantly earlier and larger post-S2 response. Each epoch length is 2 secs; the amplitude of the verticle scale is 200 microV (− up); EEG digitization rate was 200 Hz.

EXAMPLE 4

It has been demonstrated that in 7 of 7 normal human volunteers a combination of individualized psychological stress plus mild exercise results in arrhythmogenesis or ectopy (PVCs, VT) in the normal heart; these arrhythmias occur within a few minutes following recovery from exercise, during which time the dynamics of the subinterval plots (i.e. in the QT vs RR-QT plane) traverse a previously defined exclusion area, the latter of which is a dynamical zone into which the data never go with exercise alone (see plate below). Additionally, results in 20 high-risk patients with documented VT show that in 10 subjects who later manifest VF within 24-hrs, there is an excursion of the joint subinterval plots into a previously defined QT vs RR-QT exclusion area, an excursion that does not occur in either the high-risk VT controls (who lived for more than 3 years) or in the normal volunteers (with the exception noted above in which stress is superimposed upon recovery from mild exercise).

The theoretical explanation for the above findings is that any excitable-medium model will produce, during computerized simulation, premature beats, rotating spiral waves, and ventricular fibrillation (i.e. arrhythmogenesis, ectopy), but only when specific dynamical conditions are met. These dynamical conditions are known physiologically after remapping the QT and RR-QT subintervals onto the variable planes of any excitable-medium model. Three physiological predictions are made from such models each of which was satisfied in the empirical data above, (a) an exclusion area must be found in the QT vs RR-QT plane that keeps the dynamics out of a specific central region where ectopy would otherwise be evoked (i.e. mathematically), (b) a breakdown of this exclusion area must occur, as ectopy is possible in the normal heart (a breakdown under the influence of one or more factors associated with neurocardiac risk, such as psychologic stress, myocardial ischemia, etc.), and (c) cardiac arrhythmo-genesis or ectopy will occur only when the QT vs RR-QT dynamics are coaxed into the exclusion area after its breakdown.

Because the two-dimensional exclusion area requires two degrees of freedom to be drawn, its breakdown must be associated with heartbeat PD2i's<2.0. The data to support this example are shown in the schematics depicted in FIG. 7.

Figure 7:
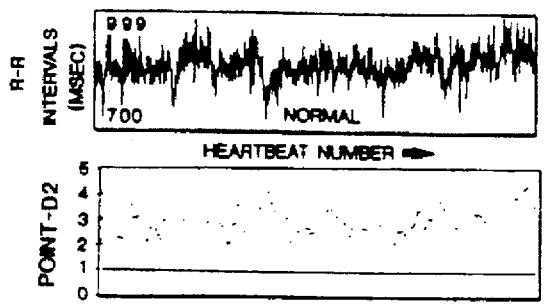
FIG. 7 is a schematics showing the prodiction of risk of arrhythmogenesis in a normal healthy heart by constructing a determinstic model subsequent to the measurement of the dimension of the heartbeat generator.
Figure 7:
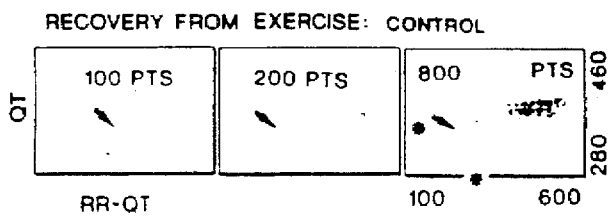
Figure 7:
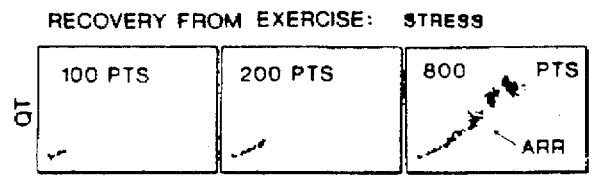
Figure 7:
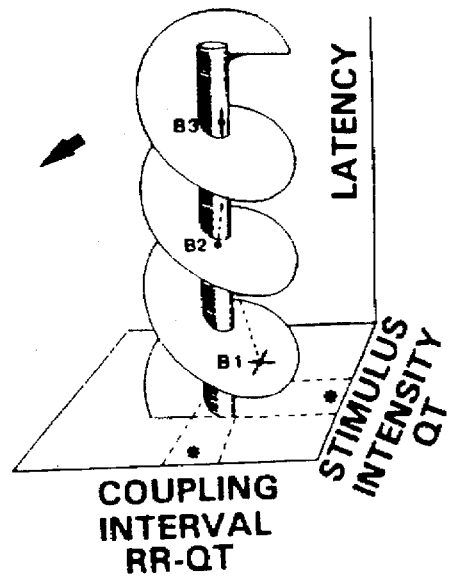
Figure 7:

The schematics shown in FIG. 7 depicts the prediction of risk of arrhythmogenesis in a normal healthy heart by constructing a deterministic model subsequent to the measurement of the dimension of the heartbeat generator. After finding that the mean dimension of the heartbeat generator was approximately 3, a modification of the 3-dimensional deterministic model of a heartbeat generator by Arthur Winfree was made, as shown at the right; it is the thickness of the shaft and the flutes near the shaft that makes this a 3-dimensional model.

The modified model predicts time-uncertainty for heartbeat points (B2, B3) falling within or near the shaft (asterisks). This predicted phenomenaon is actually observed in a joint plot of each QT (the interval between the the Q-wave and the R-wave in each heartbeat) vs RR-QT interval in the serial beats (thick arrows, upper row). To cause the heartbeat dynamics to span the 2-dimensional projection of the variable field, the subject was mildly exercised on a bicycle and then allowed to recover. Recovery time is indicated at the lower left by plotting successive numbers of heart-beat points (PTS).

In a similar experiment, but with the subject psychologically stressed by keeping him waiting for one hr while he was supposed to be somewhere else, the point-D2 of the heartbeats was reduced to 1.2, as indicated by a nearly 1-dimensional recovery trajectory. This trajectory then traveled across the previously protected area (i.e. where no points fell) and 8 premature ventricular beats were evoked. If the trajectory had landed on the "point singularity" (i.e. the infinitely thin shaft) then ventricular fibrillation would have been evoked according to the excitable-medium model. This sequence illustrates the benefit of the deterministic measure (PD2i) which can reconstruct from the data important information regarding the generator. Stochastic measures cannot reconstruct such information.

EXAMPLE 5

Figure 8:
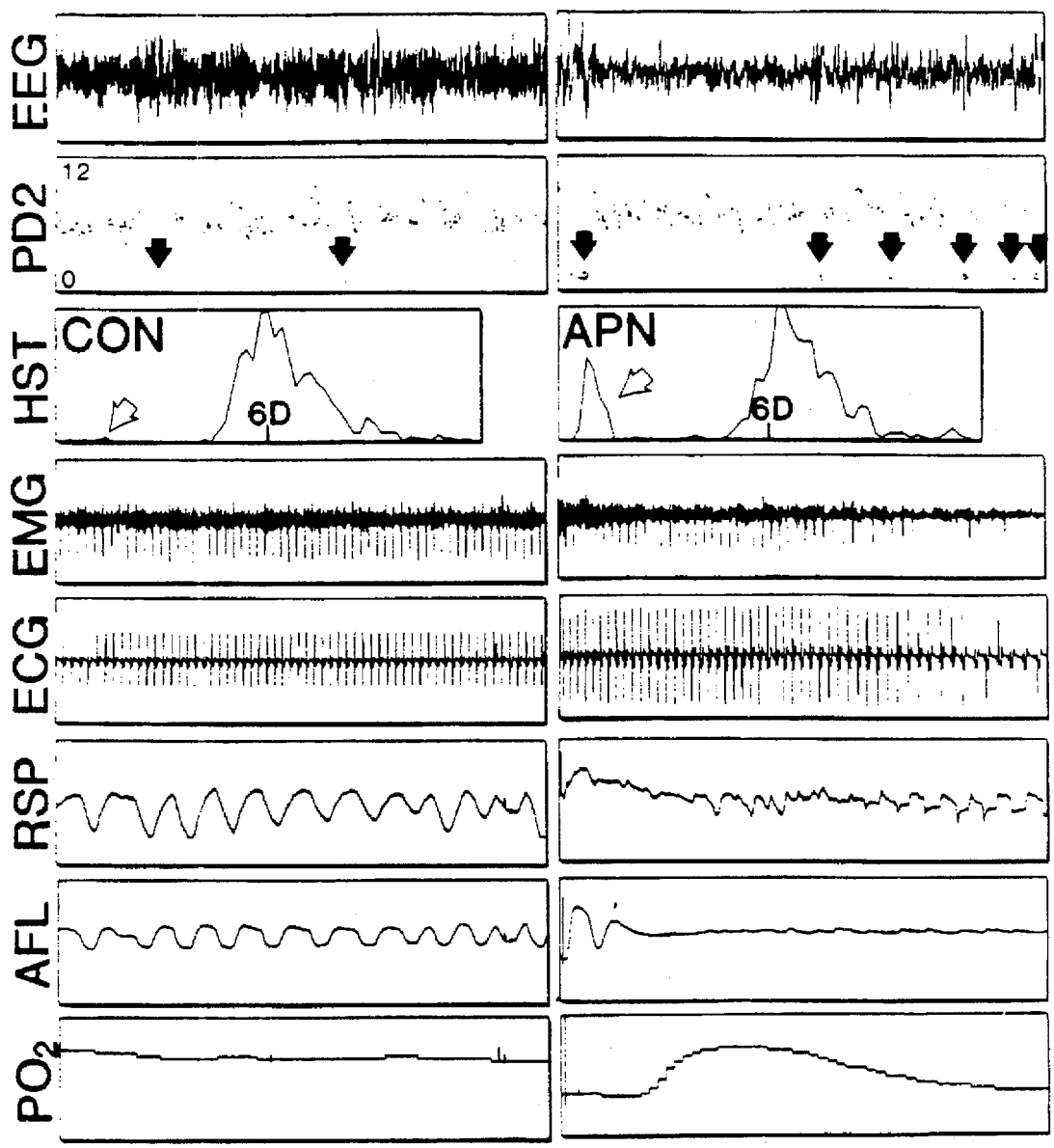
FIG. 8 shows that pathology in the sleeping EEG can be discriminated between the true sleep apnea patient and the normal control through the use of the PD2i algorithm.

In four patients with documented sleep apnea and in four normal controls, it was found that the PD2i of the sleeping EEG (Stages 1-3 of slow wave sleep) had more low-dimensional excursions in the apnea subjects than in the controls. There were no significant differences detected in the power spectrum of these same EEG records. Thus, a pathology in the sleeping EEG can be descriminated between the true sleep apnea patient and the normal control through the use of the PD2i algorithm. These data are presented in FIG. 8.

The PD2i's of the sleeping EEG of sleep apnea patients (APN) show more low-dimensional excursions (dark arrows, white arrow) than those in control subjects also presenting with a sleep disorder. The vertex electrocencephalogram (EEG), Point-D2 (PD2), histogram of PD2i's (HST), neck-muscle electromyogram (EMG), electrocardiogram (ECG), respiration (RSP), air flow (AFL) and blood $PO_2$ ($PO_2$) are shown for the control (left column) and apnea subjects (right column).

EXAMPLE 6

By attaching the output of the PD2i algorithm to a software filter that recoginizes, RR-interval PD2i's<1.2 or EEG-PD2i's from an epileptic focus with a standard deviation greater than that from a perifocal lead, an electrophysiological precursor of an untoward electrophysiological event (e.g. ventricular fibrillation or epileptic seizure) can be predicted at a time that would be soon enough for a clinician to prevent the undesireable occurrence of the event.

EXAMPLE 7

Both fatal arrhythmogenesis and hypertension are linked to the same underlying neurocardiac mechanisms: blockade of descending projections from the frontal lobes and amygdala will not only prevent ventricular fibrillation following coronary artery constriction in psychologically-stressed animals, but it will also normalize blood-pressure elevations in several animal models of experimental hypertension. Thus, neurophysiological or electrocardiac abnormalities can be detected by PD2i analyses of the MEG or ECG in hypertensive patients.

EXAMPLE 8

The present invention can also be used to determine cognitive processes. It is known through event-related potential research that there are EEG correlates of intelligence, motor performance and perception. Since the PD2i of event-related potentials is more sensitive than the event-related potential itself to certain types of perception (e.g. the alteration of perception produced by the instructional set, demonstrated in Example 3, for expectancy of "weak" and "strong" sensory stimuli that are physically the same), the PD2i of other types of event related EEG potentials, evoked in other stimulus paradigms, are more sensitive than the event-related potentials themselves to the underlying cognitive process.

EXAMPLE 9

Certain types of autonomic electrophysiological responses have been associated with lie detection. More recently the possession of secret knowledge has been revealed through analysis of event-related potential components (e.g. enhancement of the P3 component of a "target" stimulus). Because the PD2i of electrophysiological potentials regulated by both the central and autonomic nervous system has been shown to be more sensitive and specific in the detection of underlying pathology than any of a variety of stochastic analyses of the same data, it would be expected that the PD2i of electrophysiological potentials evoked in a paradigm to reveal secret knowledge would similarly be more sensitive and specific, and hence to enhance the lie-detection method.

EXAMPLE 10

In data from conscious pigs, not only did PD2i reduction show sensitivity to imminent risk of VF (as described in human patients in Example 1) but also to myocardial ischemia. Table 6 below shows that mean PD2i reduction during the first minute following complete left anterior descending coronary occlusion is indeed predictive of VF, but additionally that the PD2i reduction is monotonically reduced as a function of time following acute coronary artery occlusion, and that PD2i reduction is monotonically reduced as a function of the percent occlusion of the coronary artery. Thus, PD2i reduction is proportional to the degree of myocardial ischemia, both as it accumulates in time and as it is related to the degree of coronary artery constriction.

TABLE 6

| | Control* 0% Occ | | Partial 50% Occ | | | Severe 90% Occ | | | Complete* 100% Occ | | | | | | |
|---|---|---|---|---|---|---|---|---|---|---|---|---|---|---|---|
| | | | | | | | | | Whole Epoch | | First Min# | | Last Min# | | |
| Pig Id | Mean PD2i | SD PD2i | Mean PD2i | SD PD2i | Had VF | Mean PD2i | SD PD2i | Had VF | Mean PD2i | SD PD2i | Mean PD2i | SD PD2i | Mean PD2i | SD PD2i | Had VF |
| 1 | 3.9 | 0.84 | 2.9^ | 0.95 | no | | | | | | early VF | | | | yes |
| 2 | 3.7 | 0.82 | 3.5^ | 0.86 | no | 3.0 | 1.44 | no | | | early VF | | | | yes |
| 3 | 1.6 | 0.87 | | | | | | | 1.2 | 1.10 | 1.22 | 0.30 | 1.08 | 0.13 | yes |
| 4 | 2.0 | 1.09 | | | | | | | 1.4 | 1.11 | 1.39 | 0.34 | 1.08 | 0.14 | yes |
| 5 | 2.7 | 0.65 | 2.3 | 1.14 | no | | | | 1.7 | 1.11 | 1.60 | 0.77 | 0.93 | 0.22 | yes |
| 6 | 1.3 | 0.85 | 1.2 | 0.86 | no | | | | 1.2 | 0.86 | 1.27 | 0.44 | 0.87 | 0.19 | yes |
| 7 | 3.3 | 0.69 | | | | | | | 1.8 | 1.22 | 2.43 | 1.36 | 1.39 | 0.22 | yes |
| 8 | 1.5 | 0.67 | | | | | | | | | early VF | | | | yes |
| Mean | 2.5 | 0.81 | | | | | | | 1.4 | 1.08 | 1.58 | 0.64 | 1.07 | 0.18 | |

*Student's paired t-test, t = 6.4, df > 100, two-tailed alpha, p < .01
Student's paired t-tst, t = 7.6, df > 100, two-tailed alpha, p < .01
^Replications of the 50% occlusion experiments for pigs 1 and 2 were: 2.5, 0.81, no; 3.2, 1.56, no.

Table 6 tabulates the effects of left anterior descending coronary artery occlusion of various degrees (100%, 90%, 50%) on the mean Point-D2 of RR intervals in the conscious pig. Each pig was stressed by the unfamiliar laboratory. The control data (8.3 min) were recorded immediately before complete coronary occlusion. During complete occlusion experiments, pigs 1, 2 and 8 showed short-latency ventricular fibrillation (VF latecy: 1.0, 3.0, 1.2 min); this prevented sufficient data acquisition to calculate the PD2i. In the other pigs the VF latency was 7.0 to 11.7 minutes. After VF, the coronary occlusion was released and the heart electroconverted. Additional experiments were performed in some pigs, on separate days; both 50% and 90% occlusion experiments were performed (15 min in duration, no VF, pulsed-Doppler ultrasound assessemnt of coronary blood velocity).

After 24-hrs of recovery from the last experiment each pig was euthanized with pentobarbital and the excised heart examined for histochemical evidence of myocardial ischemia (HBFP stain) and coronary stenosis; no heart showed evidence of myocardial ischemia or any coronary anolomies, thus indicating normal myecardial conditions under which all experiments were performed.

The illustrated embodiments have proven to be useful in many applications for this art. Further modifications based on the disclosure will occur to persons skilled in the art. These modifications are within the scope and spirit of the present invention as defined by the following claims.

What is claimed is:

1. In combination in a system for detecting and predicting biological anomalies, comprising:
   (a) means for receiving electrophysiological signals;
   (b) means for amplifying and digitizing said electrophysiological signals;
   (c) means for storing a data processing routine, said data processing routine for analyzing said digitized electrophysiological signals, said routine comprised of a set of application parameters associated with biological data correlating with biological anomalies, said routine capable of processing said digitized electrophysiological signals into signals detecting and predicting the onset of said biological anomalies, wherein said routine comprises:

$$PD2i \sim \log C(n,r,nref\star)/\log r,$$

where ~ means scales as, C is the correlation integral for PD2i, in which n equals the data length, r equals the scaling range, and nref★ equals a location of the reference vector for estimating the scaling region slope of log C / log r in a restricted small log-r range that is devoid of the effects of nonstationary data, and wherein said data processing routine for analyzing said digitized electrophysiological signals, further comprises a set of parameters for defining nref★, in data in which nonstationarities exist, said parameter selected from the group consisting of parameter LC, a linearity criterion for defining the linearity of the scaling region; parameter PL, a criterion for the plot length from the smallest log-r value to the largest log-r value of the linear scaling region; parameter MS, a criterion for the minimum length of the linear scaling region; and parameter CC, a convergence criterion for the plot of the linear scaling region slope vs embedding dimension.

2. A method of detecting and predicting biological anomalies, comprising the steps of:
   (a) inputting electrophysiological signals;
   (b) amplifying and digitizing said electrophysiological signals;

(c) analyzing said digitized electrophysiological signals using a routine comprised of a set of application parameters associated with biological data correlating with said biological anomalies; and (d) processing said digitized electrophysiological signals into signals detecting and predicting the onset of said biological anomalies, wherein said data processing routine for analyzing said digitized electrophysiological signals, comprises:

$$PD2i \sim \log C(n, r, nref\star)/\log r,$$

where $\sim$ means scales as, C is the correlation integral for PD2i, in which n equals the data length, r equals the scaling range, and nref$\star$ equals a location of the reference vector for estimating the scaling region slope of log C / log r in a restricted small log-r range that is devoid of the effects of nonstationary data, and wherein said data processing routine for analyzing said digitized electrophysiological signals, further comprises a set of parameters for defining nref$\star$, in data in which nonstationarities exist, said parameter selected from the group consisting of parameter LC, a linearity criterion for defining the linearity of the scaling region; parameter PL, a criterion for the plot length from the smallest log-r value to the largest log-r value of the linear scaling region; parameter MS, a criterion for the minimum length of the linear scaling region; and parameter CC, a convergence criterion for the plot of the linear scaling region slope vs embedding dimension.

* * * * *